United States Patent
Afriat

(12) 
(10) Patent No.: US 6,328,983 B1
(45) Date of Patent: Dec. 11, 2001

(54) USE OF A SILICONE GUM TO STABILIZE ASCORBIC ACID, AND NOVEL COMPOSITIONS COMPRISING THESE COMPONENTS

(75) Inventor: Isabelle Afriat, Paris (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/408,448

(22) Filed: Sep. 29, 1999

(30) Foreign Application Priority Data

Sep. 29, 1998 (FR) .................................. 98 12156

(51) Int. Cl.[7] .............................. A61K 7/00; A61K 7/42; A61K 9/14
(52) U.S. Cl. .................. 424/401; 424/489; 424/70.12; 424/409; 424/59
(58) Field of Search .................... 424/401, 489, 424/70.12, 59, 409; 556/401

(56) References Cited

U.S. PATENT DOCUMENTS

| | | | |
|---|---|---|---|
| 5,391,373 | 2/1995 | Mausner et al. | 424/401 |
| 5,629,004 | * 5/1997 | Candau et al. | 424/401 |
| 5,710,300 | * 1/1998 | Graiver et al. | 556/401 |
| 5,891,470 | 4/1999 | Rinaldi et al. | 424/451 |
| 6,013,270 | * 1/2000 | Hargraves et al. | 424/401 |
| 6,146,664 | * 11/2000 | Siddiqui | 424/489 |

FOREIGN PATENT DOCUMENTS

| | | |
|---|---|---|
| 0 670 157 | 9/1995 | (EP) . |
| 0 672 410 | 9/1995 | (EP) . |
| 0 755 674 | 1/1997 | (EP) . |
| 94/09756 | 5/1994 | (WO) . |
| 96/24325 | 8/1996 | (WO) . |
| 98/00102 | 1/1998 | (WO) . |
| 98/34591 | 8/1998 | (WO) . |

OTHER PUBLICATIONS

"Forever Young Firming Eye Gel" Product Information Sheet N. 8739, 1999, pp. 1–4, XP002105965.

* cited by examiner

Primary Examiner—Diana Dudash
Assistant Examiner—Mina Haghighatian
(74) Attorney, Agent, or Firm—Oblon, Spivak, McClelland, Maier & Neustadt, P.C.

(57) ABSTRACT

The present invention relates to the use of a silicone gum to stabilize ascorbic acid or one of its esters or salts in a topical composition and to novel compositions comprising these components and having a pH of from 4 to 7. These compositions can be used in the fields of cosmetology, dermatology and veterinary medicine.

40 Claims, No Drawings

USE OF A SILICONE GUM TO STABILIZE ASCORBIC ACID, AND NOVEL COMPOSITIONS COMPRISING THESE COMPONENTS

BACKGROUND OF THE INVENTION

Field of the Invention

The invention relates to the use of a silicone gum to stabilize ascorbic acid and to novel compositions comprising these components and suitable for use in particular in the fields of cosmetology, dermatology and/or veterinary medicine.

The invention also relates to the use of these compositions for cosmetic treatment of the skin and for the preparation of a cream or pomade intended for dermatological treatment of the skin and/or for veterinary treatment.

The invention additionally relates to a method of cosmetic treatment which consists in applying the said compositions to the skin.

The compositions of the invention can be applied topically, to the face, including the area around the eyes, to the body, and to the scalp of human beings.

Attempts have long been made to stabilize ascorbic acid, or vitamin C, in suitable pharmaceutical presentation forms, owing to its beneficial properties.

Indeed, ascorbic acid has many biological functions, such as the stimulation of collagen synthesis, the strengthening of cutaneous tissues against external attack (UV radiation, pollution), depigmentation, anti-free radical activity, and compensation for vitamin E deficiency. Some of these beneficial properties were reported in particular by England and Seifter in the article "The biochemical functions of ascorbic acid", published in Ann. Rev. Nutri., 1986: 6, pp. 365–406.

Due to its chemical structure (alpha-keto lactone), however, ascorbic acid is very sensitive to the influence of environmental parameters such as light, oxygen and water (owing to its pH and to the presence of metal traces). Over time, ascorbic acid in solution undergoes an unavoidable degradation. Furthermore, emulsions containing ascorbic acid have a tendency to become unstable, i.e. to separate into two phases over the course of time.

Diverse treatments have been applied to this problem in the prior art.

In order to reduce or delay the degradation of ascorbic acid in solution, the authors of document US-A-5,140,043 recommended stabilizing it by introducing it into aqueous-alcoholic solutions formed of at least 80% of water and having a pH of less than 3.5.

Owing to the high acidity of the solutions, it is difficult to envisage using them in the cosmetic and/or pharmaceutical sectors.

Indeed, repeated application of these solutions may disrupt the balance of the skin and in particular may irritate or even burn the skin.

Also known is the article by B. R. Hajratwala entitled "Stability of ascorbic acid", published in Revue Sciences Pharmaceutiques, on 15 March 1985.

This article teaches in particular that ascorbic acid in acidic aqueous solution is stabilized by the addition of a surfactant which is an ethoxylated sorbitan ester.

In particular, the author reported in the article that, at a pH of 3.4 and at 25° C., the addition of this surfactant reduced the rate of oxidation, and thus the rate of degradation, of ascorbic acid in solution.

This document also teaches the use of a chelating agent such as ethylenediaminetetraacetic (EDTA), and packaging under nitrogen in the absence of light, in order to improve the stability of ascorbic acid in aqueous solution.

An acidic aqueous solution of this kind, applied to the skin, exhibits the same disadvantages as described above for acidic aqueous-alcoholic solutions. Furthermore, the stabilization obtained is still inadequate.

Further methods of stabilizing ascorbic acid have been considered, in particular by coating (technique described in document FR-A-1,600,826) or by granulation of ascorbic acid (technique illustrated in document JP-A-53-127819, for the agri-food sector).

However, these techniques are on the one hand expensive and may on the other hand adversely affect the ascorbic acid, during a heating operation, for example, and/or may lead to compositions of poor cosmetic acceptability, as is the case for granules.

It is known, moreover, for document FR-A-1,489,249 to use metal salts of phosphorylated ascorbic acid, especially magnesium ascorbylphosphate, in cosmetic compositions.

The last-mentioned compound has an activity similar to that of ascorbic acid, from which it is obtained, but has certain disadvantages which make its use on the skin fairly unlikely. In particular, since magnesium ascorbylphosphate is stable only at a basic pH (pH 8 to pH 9), it must be incorporated in a basic composition, which may be irritant to the skin (whose pH is approximately 5.5).

Document EP 0 670 157 describes an emulsion comprising an aqueous phase containing ascorbic acid and having an acidic pH of not more than 3.5.

Compositions based on polyols of carboxylic acid in combination with specific emollients and with ascorbic acid are described in document WO 98/22075. The recommended pH of these compositions is between 7 and 8.

Such acidic or basic pH values may present disadvantages.

Consequently, none of the proposals which have been made to date has provided a solution to the technical problems associated with the instability of ascorbic acid in solution in a suitable pharmaceutical form which combines efficacy and comfort for the cosmetic and/or dermatological sectors and at a cost which is compatible with industrial requirements.

The need thus remains for a composition which can be used in the cosmetic, dermatological and/or veterinary sectors and comprises stabilized ascorbic acid in the free state, i.e. without any additional group, especially a stabilizing group, and which does not cause any irritation to the skin after application.

The applicant has now surprisingly discovered that the use of a silicone gum allows ascorbic acid to be stabilized.

The advantage of using a silicone gum lies in particular in the ability to use ascorbic acid in a composition which causes neither irritation nor burning to the skin. Consequently, the composition of the invention is well received by users. Moreover, the composition of the invention has the advantage of being comfortable without being greasy.

Moreover, the fact that the composition of the invention is able to incorporate ascorbic acid in the free, protonated state provides treatments which are more effective relative to the prior art preparations comprising ascorbic acid "derivatives" which are hydrolysable in contact with the skin.

The compositions of the invention can be presented in particular in the form of milks or creams which can be used in particular in the cosmetic, dermatological and/or veterinary sectors. They have a light texture and spread well. In addition, on application, they give a sensation of freshness and impart an instantaneous glow to the complexion. In particular, they permit smoothing of the lines and imperfections of the skin.

Additionally, the compositions in accordance with the invention have the advantage that they can include any type of hydrophilic or lipophilic active agent, the pH of the compositions being neutral or weakly acidic.

Furthermore, the compositions of the invention have good stability properties, especially at room temperature (20° C.).

The present invention therefore essentially provides for the use of a silicone gum to stabilize ascorbic acid or one of its esters or salts in a topical composition.

For the purposes of the present invention, ascorbic acid, or vitamin C, means ascorbic acid in the free, protonated state or one of its esters or salts.

For the purposes of the present invention, the term "silicone gum" is applied to linear non-crosslinked polydimethyl siloxanes which may be hydroxylated or phenylated and which have the consistency of a thick oil or transparent solid, in contrast to the alkyl- and alkoxy dimethicones which, when solid, have an opaque waxy appearance, but which may also have the appearance of a clear oil when their melting point is lower than room temperature.

The silicone gum can be selected from polydiorganosiloxanes having a molecular weight of from 100,000 to 2,000,000, and, preferably, from 100,000 to 1,500,000.

These silicone gums preferably have a viscosity equal to or greater than 200,000 cSt (0.2 m²/s) and, preferably, greater than 300,000 cSt (0.3 m²/s), this viscosity being measured on a Brookfield viscometer at 25° C.

More particularly, use is made of a silicone gum selected from the silicone gums of formula (I) below:

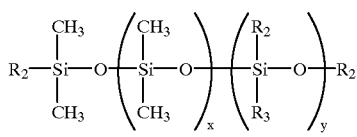

in which:

$R_2$ represents —$CH_3$, —OH or —$C_6H_5$, $R_3$ represents —$CH_3$, —OH, —$C_6H_5$ or —OSi($CH_3$)$_3$, x=0 or an integer, and y is an integer, with the proviso that y or x and y are integers such that the weight-average molecular weight is greater than 100,000 and preferably from 100,000 to 1,500,000.

The preferred silicone gums of the invention are selected from dimethicones (polydimethylsiloxanes) and dimethiconols (polydimethylsiloxanes having a terminal hydroxyl group).

The silicone gum can be employed alone or in a mixture, in particular with a solvent selected from volatile silicones, polydimethylsiloxane oils, polyphenylmethylsiloxane oils, isoparaffins, methylene chloride, pentane, dodecane, tridecane, tetradecane and mixtures thereof.

Silicone gums are generally marketed by suppliers in presolubilized or non-presolubilized form in a proportion of from 5 to 20% and, preferably, from 10 to 15% in a volatile or non-volatile linear or cyclic polydimethylsiloxane of low molecular weight.

By way of example of silicone gums, mention may be made of the dimethicone sold 96% in cyclomethicone by the company Rhone Poulenc under the name "Mirasil DM-500000®" and the dimethicone sold by the company Wacker under the name "AK 300000®", and the dimethiconols sold under the names "Q2-1403®", "Q2-1401®" and "Q2-1503®" by the company Dow Corning.

The invention also provides a topical composition in the form of an emulsion comprising ascorbic acid or one of its esters or salts, a silicone gum and a silicon-containing emulsifier and having a pH of between 4 and 7, preferably between 5.5 and 6.5.

The compositions according to the invention can consist in particular of a water-in-oil or oil-in-water emulsion.

The silicone gums are those described above.

Likewise, the silicone gum can be employed alone or in a mixture with a solvent selected from volatile silicones, polydimethylsiloxane oils, polyphenylmethylsiloxane oils and mixtures thereof.

Ascorbic acid or one of its esters is present in the compositions of the invention in a concentration ranging from 0.1 to 20% and, preferably, from 2 to 10% by weight relative to the total weight of the composition.

The silicone gum is present in the compositions of the invention in an active-substance concentration ranging from 1 to 20% and, preferably, from 2 to 15% by weight relative to the total weight of the composition.

In a particularly preferred embodiment of the invention, the composition additionally comprises at least one polyol.

The polyol can be selected from glycerol, sorbitol and glycols, especially propylene glycol, butylene glycol and polyethylene glycols.

According to a particular embodiment of the invention, the polyol or polyols is or are totally or partly in a form in which they are complexed with an acrylic or methacrylic polymer. The polymer may also include bound water; that is, it can be complexed with a mixture of water and polyol(s).

By acrylic or methacrylic polymer is meant a homopolymer or copolymer of acrylic or methacrylic acid or a homopolymer or copolymer of a derivative of acrylic or methacrylic acid.

As homopolymers which complex water and polyols, mention may be made of those homopolymers sold under the names Norgel and Lubrajel CG by the company Guardian. These polymers are polyglyceryl acrylates complexed with more than 65% of glycerol and/or propylene glycol and less than 35% by weight of bound water. These polymers provide the complexed polyol and water and may also act as a gelling agent for the composition.

The polyol can be present in a concentration ranging from 5 to 40% and, preferably, from 15 to 30% by weight relative to the total weight of the composition.

The compositions according to the invention may additionally comprise at least one silicone oil.

These oils can be selected in particular from the group consisting of volatile silicones such as cyclopentadimethylsiloxane and cyclotetradimethyl-siloxane, polydimethylsiloxanes, polyphenyltrimethyl-siloxanes and fluorinated silicones.

The silicone oil may be present in a concentration ranging from 2 to 40% and, preferably, from 10 to 35% by weight relative to the total weight of the composition.

The compositions according to the invention additionally comprise at least one silicon-containing emulsifier.

The silicon-containing emulsifiers may be selected from dimethicone copolyols and alkyldimethicone copolyols. As emulsifiers which can be used in the compositions of the invention, mention may be made of the polyglyceryl-4 isostearate/cetyldimethicone copolyol/hexyl laurate mixture sold under the name "Abil WE 09®" by the company Goldschmidt, the cetyldimethicone copolyol sold under the name "Abil EM 90®" by the company Goldschmidt, and the cyclomethicone/dimethicone copolyol mixture sold under the name "Q2-3225C" or "Q2-5225C" by the company Dow Corning.

According to a preferred embodiment of the invention, use is made of an alkyldimethicone copolyol and, in particular, cetyldimethicone copolyol. The emulsifier is present in an amount ranging preferably from 0.1 to 10% and, more preferably, from 0.5 to 5% of the total weight of the composition.

The compositions according to the invention may additionally comprise one or more fats selected in particular from silicone resins or waxes, fluorinated oils, oils of animal origin, oils of plant origin, mineral oils and synthetic oils.

Waxes which can be used are, in particular, silicone waxes such as alkoxydimethylsiloxanes, and more particularly stearoxypolydimethylsiloxanes, alkylpolysiloxanes and polydimethylsiloxanes having a mercapto function.

Resins which can be used are, in particular, silicone resins such as trimethylsiloxysilicates.

Conventionally, the composition of the invention may also comprise adjuvants which are common in the fields of cosmetology and dermatology, such as surfactants, especially foaming surfactants, hydrophilic or lipophilic active agents in addition to ascorbic acid, preservatives, antioxidants, solvents, perfumes, fillers, screening agents, odour absorbers, colorants and lipid vesicles. The amounts of these various adjuvants are those which are conventionally employed in the fields in question, and are for example from 0.01% to 15% of the total weight of the composition.

Examples of hydrophilic active agents which can be used are proteins or protein hydrolysates, amino acids, allantoin, sugar and sugar derivatives, starch, hyaluronic acid, and plant extracts, such as Ginkgo biloba or ginseng extracts.

Examples of lipophilic active agents which can be used are tocopherol (vitamin E) and its derivatives, essential fatty acids, ceramides and essential oils.

Fillers which may be mentioned are nylon powder and microspheres (acrylate copolymers).

The compositions according to the invention may therefore constitute a cosmetic and/or dermatological composition.

The invention also provides for the use of the above composition for a cosmetic treatment of the skin with a view, in particular, to toning it, regenerating it, smoothing out the lines and/or wrinkles of the skin, lightening the complexion, removing pigmentary blemishes from the skin, and/or combating the damage done by UV radiation, and/or strengthening the cutaneous tissues against environmental attack (pollution).

The invention additionally provides for the use of an above composition for the preparation of a cream intended for dermatological and/or veterinary treatment.

Finally, the invention provides a method of cosmetic treatment which consists in applying to the skin, including the area around the eyes, a composition according to the invention.

Other advantages and features of the invention will appear more clearly on reading the following examples, which are given by way of illustration and not of limitation.

EXAMPLE 1

Water-in Oil Emulsion

Phase A

| Demineralized water | 25.05% |
|---|---|
| Glycerol | 24% |
| Propylene glycol | 7% |
| Preservative | 0.2% |
| Vitamin C | 5% |
| Magnesium sulphate | 2% |
| Acrylate copolymers (microspheres) | 0.75% |

Phase B

| DC2 5225C (silicon-containing emulsifier in silicone oil) | 8% |
|---|---|
| Silicone oil, 20 cSt | 23% |
| Silicone AK 300000 (silicone gum) | 5% |

The procedure for preparing this composition is as follows: Each phase is prepared separately, and phase A is introduced into phase B with stirring.

This gives a stable, bright white cream. This composition is suitable for smoothing facial lines in the skin and for making the complexion glow.

EXAMPLE 2

Water-in Oil Emulsion

Phase A

| Demineralized water | 25.05% |
|---|---|
| Glycerol | 24% |
| Propylene glycol | 7% |
| Preservative | 0.2% |
| Vitamin C | 5% |
| Magnesium sulphate | 2% |
| Acrylate copolymers | 0.75% |

Phase B

| Cetyldimethicone copolyol (Abil EM90) | 0.8% |
|---|---|
| Silicone oil, 20 cSt | 23% |
| Cyclomethicone | 7.2% |
| AK 300000 (silicone gum) | 5% |

The procedure is the same as in Example 1.

This gives a stable, bright white cream. This composition is suitable for smoothing facial lines in the skin and for making the complexion glow.

COMPARATIVE EXAMPLE 2

Water-in Oil Emulsion

Phase A

| Demineralized water | 25.05% |
|---|---|
| Glycerol | 24% |
| Propylene glycol | 7% |

-continued

|  |  |
|---|---|
| Preservative | 0.2% |
| Vitamin C | 5% |
| Magnesium sulphate | 2% |
| Acrylate copolymers | 0.75% |

Phase B

|  |  |
|---|---|
| Cetyldimethicone copolyol (Abil EM90) | 0.8% |
| Silicone oil, 20 cSt | 28% |
| Cyclomethicone | 7.2% |

The procedure is the same as in Example 1.

This gives a thick cream which is unstable and quickly separates into two phases.

EXAMPLE 3

Water-in Oil Emulsion

Phase A

|  |  |
|---|---|
| Demineralized water | 20% |
| Glycerol | 24% |
| Propylene glycol | 13% |
| Vitamin C | 5% |
| Magnesium sulphate | 2% |

Phase B

|  |  |
|---|---|
| Cetyldimethicone copolyol (Abil EM90) | 0.8% |
| Silicone oil | 30.2% |
| Mirasol DM-500000 (silicone gum) | 5% |

The procedure is exactly the same as in Example 1.

This gives a stable, white cream which is suitable for smoothing facial lines in the skin and for making the complexion glow.

What is claimed is:

1. A method for stabilizing ascorbic acid or one of its esters or salts in a water-containing topical composition, comprising incorporating therein an ascorbic acid-stabilizing amount of a silicone gum.

2. The method according to claim 1, characterized in that the silicone gum is selected from polydiorganosiloxanes having a molecular weight of from 100,000 to 2,000,000.

3. The method according to claim 2, wherein the polydiorganosiloxanes have a molecular weight of from 100,000 to 1,500,000.

4. The method according to claim 1, characterized in that the silicone gum has a viscosity equal to or greater than 0.2 m²/s.

5. The method according to claim 1, characterized in that the silicone gum has a viscosity equal to or greater than 0.3 m²/s.

6. The method according to claim 1, characterized in that the silicone gum is selected from the silicone gums of formula (I) below:

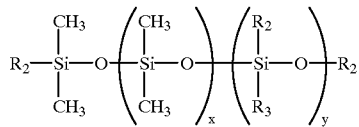

in which:

$R_2$ represents —$CH_3$, —OH or —$C_6H_5$, $R_3$ represents —$CH_3$, —OH, —$C_6H_5$ or —$OSi(CH_3)_3$, x=0 or an integer, and y is an integer, with the proviso that y or x plus y are integers such that the weight-average molecular weight is greater than 100,000.

7. The method according to claim 6, wherein the weight-average molecular weight of the silicone gum is from 100,000 to 1,500,000.

8. The method according to claim 1, characterized in that the silicone gum is selected from dimethicones and dimethiconols.

9. The method according to claim 1, characterized in that the silicone gum is employed alone or in a mixture with a solvent selected from the group consisting of volatile silicones, polydimethylsiloxane oils, polyphenylmethylsiloxane oils and mixtures thereof.

10. Topical composition in the form of an emulsion, which comprises ascorbic acid or one of its esters or salts, a silicone gum in an ascorbic acid-stabilizing amount, and a silicon-containing emulsifier, wherein the composition has a pH of from 4 to 7.

11. Composition according to claim 10, characterized in that the silicone gum is selected form polydiorganosiloxanes having a molecular weight of from 100,000 to 2,000,000.

12. Composite according to claim 11, wherein the molecular weight is from 100,000 to 1,500,000.

13. Composition according to claim 10, characterized in that the silicone gum has a viscosity equal to or greater than 0.2 m²/s.

14. Composition according to claim 10, characterized in that the silicone gum has a viscosity equal to or greater than 0.3 m²/s.

15. Composition according to claim 10, characterized in that the silicone gum is selected from the silicone gums of formula (I) below:

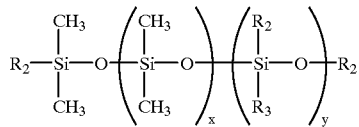

in which $R_2$ represents —$CH_3$, —OH or —$C_6H_5$, $R_3$ represents —$CH_3$, —OH, —$C_6H_5$ or —$OSi(CH_3)_3$, x=0 or an integer, and y is an integer, with the proviso that y or x plus y are integers such that the weight-average molecular weight is greater than 100,000.

16. Composition according to claim 15, wherein the weight-average molecular weight is from 100,000 to 1,500,000.

17. Composition according to claim 10, characterized in that the silicone gum is selected from the group consisting of dimethicones and dimethiconols.

18. Composition according to claim 10, characterized in that the silicone gum is employed alone or in a mixture with a solvent selected from the group consisting of volatile silicones, polydimethylsiloxane oils, polyphenylmethylsiloxane oils and mixtures thereof.

19. Composition according to claim 10, characterized in that ascorbic acid or one of its esters or salts is present in a concentration ranging from 0.1 to 20% relative to the total weight of the composition.

20. Composition according to claim 10, characterized in that ascorbic acid or one of its esters or salts is present in a concentration ranging from 2 to 10% relative to the total weight of the composition.

21. Composition according to claim 10, characterized in that the silicone gum is present in an active-substance concentration ranging from 1 to 20% by weight relative to the total weight of the composition.

22. Composition according to claim 10, characterized in that the silicone gum is present in an active-substance concentration ranging from 2 to 15% by weight relative to the total weight of the composition.

23. Composition according to claim 10, characterized in that the composition additionally comprises at least one polyol.

24. Composition according to claim 23, characterized in that the polyol is selected from the group consisting of glycerol, sorbitol and glycols.

25. Composition according to claim 23, characterized in that the polyol is present in a concentration ranging from 5 to 40% by weight relative to the total weight of the composition.

26. Composition according to claim 23, characterized in that the polyol is present in a concentration ranging from 15 to 30% by weight relative to the total weight of the composition.

27. Composition according to claim 10, characterized in that the composition additionally comprises at least one silicone oil.

28. Composition according to claim 27, characterized in that the silicone oil is selected from the group consisting of volatile silicones, polydimethylsiloxanes. polyphenyltrimethylsiloxanes and fluorinated silicones.

29. Composition according to claim 27, characterized in that the silicone oil is present in a concentration ranging from 2 to 40% by weight relative to the total weight of the composition.

30. Composition according to claim 27, characterized in that the silicone oil is present in a concentration ranging from 10 to 35% by weight relative to the total weight of the composition.

31. Composition according to claim 10, characterized in that the silicon-containing emulsifier is a dimethicone copolyol or an akyldimethicone copolyol.

32. Composition according to claim 10, characterized in that the emulsifier is present in a concentration ranging from 0.1 to 10% by weight relative to the total weight of the composition.

33. Composition according to claim 10, characterized in that the emulsifier is present in a concentration ranging from 0.5 to 5% by weight relative to the total weight of the composition.

34. Composition according to claim 10, characterized in that it additionally comprises one or more fats selected from the group consisting of silicone resins, silicone waxes, fluorinated oils, oils of animal origin, oils of plant origin, mineral oils and synthetic oils.

35. Composition according to claim 10, characterized in that it comprises at least one adjuvant selected from surfactants, hydrophilic or lipophilic active agents, preservatives, antioxidants, solvents, perfumes, fillers, screening agents, odor absorbers, colorants, lipid vesicles or mixtures thereof.

36. Composition according to claim 10, characterized in that it consists of a water-in-oil or oil-in-water emulsion.

37. Composition according to claim 10, characterized in that it constitutes a cosmetic or dermatological composition.

38. A method for at least one of cosmetic treatment of the skin for toning it and regenerating it, smoothing out the lines or wrinkles or lines and wrinkles of the skin, lightening the complexion, removing pigmentary blemishes from the skin, combating the damage done by UV radiation, and strengthening the cutaneous tissues against environmental attack, comprising applying to the skin a composition according to claim 10.

39. A method for dermatological or veterinary treatment, comprising applying to an area of skin in need of dermatological or veterinary treatment, respectively, the composition according to claim 10 in the form of a cream.

40. A method of cosmetic treatment, comprising applying to the area around the eyes, a composition according to claim 10.

* * * * *

UNITED STATES PATENT AND TRADEMARK OFFICE
CERTIFICATE OF CORRECTION

PATENT NO. : 6,328,983 B1  Page 1 of 1
DATED : December 11, 2001
INVENTOR(S) : Afriat, Isabelle It is certified that error appears in the above-identified patent and that said Letters Patent is hereby corrected as shown below:

<u>Column 8,</u>
Line 32, "selected form" should read -- selected from --.

<u>Column 10,</u>
Line 3, "akyldimethicone" should read -- alkyldimethicone --.

Signed and Sealed this

Twenty-sixth Day of March, 2002

Attest:

JAMES E. ROGAN
Attesting Officer  Director of the United States Patent and Trademark Office